(12) United States Patent
Dobrovolsky et al.

(10) Patent No.: US 11,426,477 B2
(45) Date of Patent: Aug. 30, 2022

(54) SYSTEMS AND METHODS FOR UV DECONTAMINATION OF RESPIRATORS

(71) Applicant: Amplify Solutions, Inc., Cincinnati, OH (US)

(72) Inventors: Sasha Dobrovolsky, Nashville, TN (US); Mark Giller, Maineville, OH (US)

(73) Assignee: Amplify Solutions, Inc., Cincinnati, OH (US)

( * ) Notice: Subject to any disclaimer, the term of this patent is extended or adjusted under 35 U.S.C. 154(b) by 0 days.

(21) Appl. No.: 17/356,383

(22) Filed: Jun. 23, 2021

(65) Prior Publication Data

US 2021/0402026 A1 Dec. 30, 2021

Related U.S. Application Data

(60) Provisional application No. 63/043,446, filed on Jun. 24, 2020.

(51) Int. Cl.
*A61L 2/10* (2006.01)
*A62B 23/02* (2006.01)
*A61L 2/24* (2006.01)

(52) U.S. Cl.
CPC ............. *A61L 2/10* (2013.01); *A61L 2202/11* (2013.01); *A61L 2202/14* (2013.01); *A61L 2202/24* (2013.01); *A62B 23/025* (2013.01)

(58) Field of Classification Search
None
See application file for complete search history.

(56) References Cited

U.S. PATENT DOCUMENTS

| 4,698,206 | A | * | 10/1987 | Nevin | ....................... A61L 2/10 |
| | | | | | 422/186.3 |
| 4,952,812 | A | * | 8/1990 | Miripol | ................. A61L 2/0011 |
| | | | | | 250/455.11 |
| 9,498,551 | B2 | | 11/2016 | Yanke | |

(Continued)

FOREIGN PATENT DOCUMENTS

| AU | 2020100584 A4 | * | 5/2020 |
| CN | 106143549 A | | 11/2016 |
| KR | 10-2011-0098394 A | | 9/2011 |

OTHER PUBLICATIONS

Avon company ReadyDock using UV light to sanitize surgical masks amid COVID-19 pandemic, Mar. 30, 2020, uploaded by FOX 61, Youtube, https://www.youtube.com/watch?v=rBK-yNeUsSY, screenshot and transcript attached (Year: 2020).*

(Continued)

*Primary Examiner* — Holly Kipouros
(74) *Attorney, Agent, or Firm* — Morrison & Foerster LLP

(57) ABSTRACT

A filtering facepiece respirator decontamination device includes an enclosure defining a UV irradiation chamber, at least one UV lamp positioned in the irradiation chamber, a moveable drawer comprising a platform for positioning a respirator, wherein the moveable drawer can move to a closed position in the respirator positioned on the platform is located in the irradiation chamber, a switch for detecting that the drawer is in the closed position, and a controller for activating the at least one UV lamp based on the switch detecting that the drawer is in the closed position.

15 Claims, 10 Drawing Sheets

(56) References Cited

U.S. PATENT DOCUMENTS

| | | | | |
|---|---|---|---|---|
| 2003/0219354 | A1* | 11/2003 | Hlavinka | A61K 35/18 |
| | | | | 422/22 |
| 2012/0315187 | A1* | 12/2012 | Hermiz | A61L 2/18 |
| | | | | 422/292 |
| 2017/0202988 | A1* | 7/2017 | Clark | A61L 2/26 |
| 2018/0318457 | A1* | 11/2018 | Lucio | A61L 2/10 |
| 2020/0129650 | A1* | 4/2020 | Kim | A62B 23/025 |
| 2020/0368380 | A1* | 11/2020 | Levy | B65D 81/18 |
| 2020/0397931 | A1* | 12/2020 | Church | A61L 2/26 |
| 2021/0299304 | A1* | 9/2021 | Concannon | A61L 2/26 |
| 2021/0308495 | A1* | 10/2021 | Kersey | A61L 2/10 |
| 2021/0353798 | A1* | 11/2021 | Spear | A45F 5/021 |
| 2021/0361798 | A1* | 11/2021 | Eng | A61L 2/24 |

OTHER PUBLICATIONS

Huber et al., Principles and Practice of SARS-CoV-2 Decontamination of N95 Masks with UV-C, Jun. 9, 2020, medRxiv, pp. 12-14 (Year: 2020).*

International Search Report and Written Opinion dated Oct. 15, 2021, directed to International Application No. PCT/US2021/038747; 14 pages.

* cited by examiner

Section B-B

Section A-A

Section E-E

SYSTEMS AND METHODS FOR UV DECONTAMINATION OF RESPIRATORS

CROSS-REFERENCE TO RELATED APPLICATIONS

This application claims the benefit of U.S. Provisional Application No. 63/043,446, filed Jun. 24, 2020, the entire contents of which are incorporated herein by reference.

FIELD

This disclosure is related generally to decontamination of personal protective equipment and, more specifically, to decontamination of respirators.

BACKGROUND

Filtering Facepiece respirators (FFRs) are respiratory protective devices designed to cover the nose and mouth and achieve a close facial fit and efficient filtration of airborne particles. An N95 respirator is a disposable FFR that blocks at least 95 percent of small (0.3 micron) test particles. N95 respirators are worn by health care personnel during patient encounters to protect both the patient and health care personnel from the transfer of microorganisms, body fluids, and particulate material. The surfaces of an N95 respirator may become contaminated while filtering the inhalation air of the wearer during exposures to pathogen-laden aerosols. The pathogens on the filter materials of an N95 respirator may be transferred to the wearer upon contact with the respirator during activities such as adjusting the respirator, doffing the respirator improperly, and performing a user-seal check when redoffing a previously worn respirator. To mitigate the risk of infection from pathogens accumulating on the filter materials, N95 respirators are intended to be discarded after a single patient encounter and, thus, are commonly referred to a single-use respirators.

In the midst of a pandemic, such as the COVID-19 pandemic, the supply chain for respiratory protective devices, such as N95 respirators, can be substantially stressed due to demand exceeding supply. During shortages of respirators, healthcare facilities may choose to re-use single use N95 respirators under the recommendation of government agencies, such as the CDC. To mitigate the contact transfer of pathogens from the respirator to the wearer during reuse during the COVID-19 pandemic, for example, the CDC recommended issuing five respirators to each healthcare worker who may care for patients with suspected or confirmed COVID-19. The healthcare worker wears one respirator each day and stores it in a breathable paper bag at the end of each shift. The order of respirator use is repeated with a minimum of five days between each respirator use. However, this strategy poses significant risks due to the potential build-up of pathogens over the course of a day.

SUMMARY

According to various embodiments, a counter-top decontamination system is configured for a wearer to personally reduce the pathogen contamination on their own respirator multiple times throughout a day, for example while the wearer is taking other protective sanitation actions such as hand-washing, hand sanitizer use, or changing gloves. According to some embodiments, the decontamination device delivers an effective dose of ultraviolet (UV) light to the exterior surfaces of both sides of the respirator, including the straps, in a short period of time.

According to various embodiments, a filtering facepiece respirator decontamination device includes an enclosure defining a UV irradiation chamber; at least one UV lamp positioned in the irradiation chamber; a moveable drawer comprising a platform for positioning a respirator, wherein the moveable drawer can move to a closed position in the respirator positioned on the platform is located in the irradiation chamber; a switch for detecting that the drawer is in the closed position; and a controller for activating the at least one UV lamp based on the switch detecting that the drawer is in the closed position.

In any of these embodiments, the at least one UV lamp can include a first set of UV lamps positioned beneath the drawer and a second set of UV lamps positioned above the drawer.

In any of these embodiments, the device can include at least one reflector surrounding at least a portion of the at least one UV lamp for reflecting UV light toward the respirator.

In any of these embodiments, the platform can include a plurality of quartz rods.

In any of these embodiments, the drawer can include a plurality of quartz posts that project from the platform for locating straps of the respirator.

In any of these embodiments, the device can be configured to decontaminate a single respirator at a time.

In any of these embodiments, the device can be configured to deliver a UV dosage the respirator of 1 J/cm2 in one minute or less.

In any of these embodiments, the controller can be configured to activate the at least one UV lamp automatically in response to receiving a signal from the detector indicating that the drawer is in the closed position.

In any of these embodiments, the controller can be configured to deactivate the at least one UV lamp automatically in response to receiving a signal from the detector indicating that the drawer has moved away from the closed position.

In any of these embodiments, the enclosure can include a front aperture that is shaped to indicate the proper positioning of a respirator on the platform.

In any of these embodiments, the at least one UV lamp can be configured for generating UVC light.

According to various embodiments, a method of decontaminating a filtering facepiece respirator includes positioning the respirator on the platform of a drawer of a decontamination device; closing the drawer; activating, by the device, one or more UV lamps of the device based on the device detecting that the drawer has been closed; and deactivating, by the device, the one or more UV lamps after a pre-programmed decontamination period has elapsed.

In any of these embodiments, the method can include delivering a dosage of UV light of 1 J/cm2 to the respirator.

In any of these embodiments, the pre-programmed decontamination period can be a minute or less.

In any of these embodiments, the method can further include, in response to detecting that the drawer has been opened while the one or more UV lamps are activated, automatically deactivating the one or more UV lamps.

In any of these embodiments, the UV lamps can be configured to generate UVC light.

BRIEF DESCRIPTION OF THE DRAWINGS

The invention will now be described, by way of example only, with reference to the accompanying drawings, in which.

DETAILED DESCRIPTION

Figure 1:
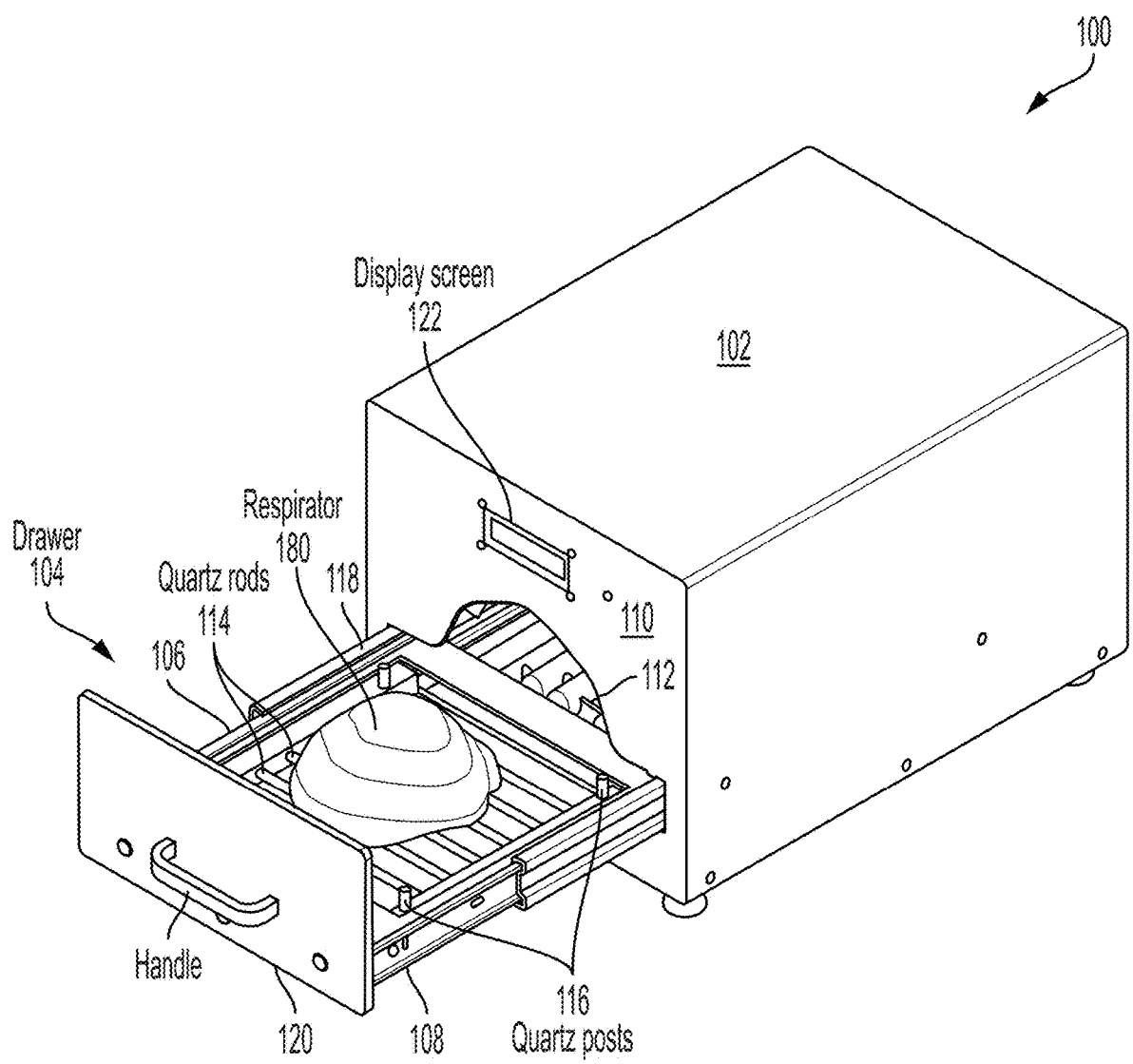
FIG. 1 illustrates a respirator decontaminate device, according to some embodiments.

Systems and methods, according to various embodiments, include a UV device that is configured irradiate a filtering facepiece respirator (referred to herein as simply a respirator), such as an N95 respirator, with UV light to deactivate pathogens that have accumulated on the respirator during use. The UV device includes a platform for positioning at least one respirator and a plurality of UV lamps positioned around the platform for irradiating the respirator with UV light. A wearer may easily place his or her own respirator in the device and initiate a decontamination cycle during which the respirator is irradiated with a sufficient amount of UV light to deactivate one or more target pathogens on the respirator. The decontamination cycle time may be relatively short, enabling a wearer to quickly and easily decontaminate the wearer's respirator, which can encourage wearers to decontaminate their respirators multiple times throughout their shift. By enabling multiple decontaminations throughout a wearer's shift, the UV device can prevent the excessive accumulation of pathogens on a wearer's respirator that can occur when respirator re-use is needed, such as during respirator shortages.

According to various embodiments, the respirator decontamination system includes an enclosure and a UV irradiation chamber within the enclosure for positioning a respirator for UV irradiation. The chamber includes a platform for supporting the respirator and a plurality of UV lamps arrayed around the chamber such that UV light from the lamps reaches substantially of the exterior surfaces of the respirator. In some embodiments, one or more UV lamps are positioned below the platform and one or more UV lamps are positioned above the platform. In some embodiments, one or more reflectors or reflective surfaces are positioned outwardly of the UV lamps to reflect UV light toward the respirator in the center of the chamber. In some embodiments, the UV lamps and reflectors are positioned to ensure that there is no shadowing—that substantially all of the external surface of the respirator, including the straps, are simultaneously irradiating with UV light.

In some embodiments, the platform is a movable platform that can be moved outwardly from the enclosure to enable a user to easily place the user's respirator on the platform. For example, the platform may be a portion of a drawer that slides out to enable access to the platform by the user. In some embodiments, the platform includes a grating for supporting the respirator and allowing light to pass through the platform to the respirator from lamps located beneath the respirator. In some embodiments, the grating is a plurality of parallel members that are substantially transparent to the UV light, or to at least a band of UV light used to decontaminate the respirator. For example, in some embodiments, the parallel members are quartz rods. In some embodiments, the platform includes strap positioning features for positioning the straps of a respirator in repeatable positions that ensure that the straps do not fold on themselves or cover the respirator body, which would otherwise cause shadowing. In some embodiments, the strap positioning features are posts, such as made of quartz, that project upwardly from the platform.

The enclosure may include a front aperture that is configured so that one or more respirators can move into and out of the enclosure as the drawer is moved in and out. The drawer can include a front panel that covers the aperture when the drawer is in a closed position so that UV light does not escape the enclosure. In some embodiments, the device includes a detector that detects when the drawer is in its closed position. Operation of the UV lamps may be based on the detector detecting whether the drawer is in the closed position. For example, the UV lamps may be disabled when the detector detects that the drawer is not in its closed position. In some embodiments, the detector can be any suitable sensor and/or switch, including a Hall Effect sensor or a limit switch.

According to various embodiments, the respirator decontamination system can be configured to irradiate a respirator with UV light for a predefined decontamination cycle time that is preselected to provide at least the UV dosage that testing has shown to be sufficiently effective at destroying or deactivating one or more target pathogens on the exterior surfaces of the respirators. For example, the UV dosage provided during a decontamination cycle may be sufficient to provide at least a 3-log reduction in one or more target viruses, such as SARS-CoV-2, accumulated on the respirator. The cycle time is generally inversely proportional to the power of the UV lamps such that embodiments with higher power lamps may have shorter decontamination cycles than embodiments with lower power lamps.

According to various embodiments, the respirator decontamination system is used by opening the drawer, positioning the respirator on the platform of the drawer, and closing the drawer. The device may then enter a decontamination cycle, for example, either automatically in response to detecting that the drawer has been closed and/or in response to a user input. Upon initiation of the decontamination cycle, the lamps may be activated and remain activated for the predefined cycle time, such as a minute or less. In some embodiments, the device may be configured to shut off the lamps upon detecting that the drawer has been opened, such as to prevent exposure of the user to UV light. Upon expiration of the cycle time, the lamps may be deactivated. The device may provide an indication to the user that the decontamination cycle is complete, and in response, the user may open the drawer and remove the decontaminated respirator. The user may then don the respirator and go about their work. Thus, the respirator decontamination system can be used by a wearer to quickly and easily decontaminate the wearer's own respirator, enabling the wearer to decontaminate their respirator multiple times throughout their shift.

During a shortage of respirators, such as during the COVID-19 pandemic, emergency use guidance (such as issued by the CDC) allowed the re-use and rationing of respirators. However, re-use and rationing can result in the same respirator being worn for many hours and over many patient interactions. Such long term wear can lead to high pathogen loads occurring on the patient-facing surface of the respirator, posing a high risk for both the wearer and patients. According to various embodiments, the respirator decontamination system allows the wearer (such as healthcare personnel) to personally reduce the bioburden on their own respirator after each patient visit (or regularly throughout the day) with minimal risk and while establishing similar benefits for the wearer and patients as the standard of care during non-emergency periods, which includes using a new respirator after each patient visit/interaction.

As used herein, a filtering facepiece respirator is a negative pressure particulate respirator with a filter as an integral part of the facepiece or with the entire facepiece composed of the filtering medium. According to various embodiments, a decontamination system according to the principles described herein can be used and/or configured to decontaminate filtering facepiece respirators of any type and/or any model, including N95 respirators, KN95 respirators, and FFP2 masks. According to various embodiments, the decontamination system can be used and/or configured for decontaminating devices other than respirators, including surgical masks, mobile phones, pagers, remote controls, writing utensils, keys, gloves, stethoscopes, and any other device that can be placed in the decontaminator.

In some embodiments, the decontamination system can be configured to perform the decontamination process differently for different types and/or models of devices. For example, the decontamination system may deliver a lower dose of UV light for a device with hard surfaces, such as a mobile phone, than a device with porous surfaces, such as a respirator. In some embodiments, the decontamination system may deliver a different dosage depending on the model of the respirator.

The decontamination system can determine the types of device in various ways. In some embodiments, the decontamination system includes a user interface for a user to input a type of device. For example, a user can navigate through a list of devices via the user interface, with each devices in the list having an associated preprogrammed decontamination process. Any suitable user interface can be used, including, for example, a touch screen, an app on a smartphone that is communicatively coupled to the decontamination system, voice commands, or gestures. In some embodiments, the UV dosage provided during a decontamination cycle may be user-selectable along with or irrespective of differences in device type. For example, the user may select a low, medium, or high dosage setting, resulting in different dosages pre-programmed into the decontamination system. In some embodiments, different decontamination cycles can be selectable for different purposes. For example, the decontamination system may be pre-programmed with decontamination cycles for sanitizing, bioburden reduction, decontamination, sterilization, etc. According to some embodiments, the availability of decontamination cycle options such as these could be determined by the user, or may be required by policy (such as of the medical facility), by regulation, or by the device configuration.

In some embodiments, the decontamination system can automatically detect a type and/or model of a device to be decontaminated using, for example, feature recognition on one or more images generated by a camera of the decontamination system, by a bar code scanner, by an RFID reader, or any other suitable method. In some embodiments, a camera may be positioned in the decontamination system for imaging a device placed therein and one or more images of the device can be analyzed using image processing to detect the type of device. The decontamination system may then execute a decontamination process that is based on the type of device. In some embodiments, the type and/or model of the device may be indicated on a display of the decontamination system for confirmation by the user. In some embodiments, the decontamination system may prevent execution of a decontamination cycle and/or may provide a warning based on its determination of the device model and/or type. For example, the decontamination system may be configured to not decontaminate and/or provide a warning when an unapproved respirator model is placed in the device. In some embodiments, the decontamination system may be configured to detect soiling or damage to a respirator and may provide a warning and/or may block execution of a decontamination cycle.

According to various embodiments, the decontamination system can be configured to perform different decontamination procedures, such as for different types of respirators and/or for different types of devices, as discussed above. Differences between decontamination procedures can include different amounts of time for which the UV lights are active, different operating power for one or more UV lights, different combinations of UV light activations (for example, only a subset of the UV lights active), or any combination of these.

According to various embodiments, individual UV light sources can power on for various time periods, such as to optimize the uniformity of the UV dose or to target higher dosage in certain areas (for example to address shadowing). In some embodiments, one or more UV light sources can move to a different position, such as to deliver uniform dosage or target specific areas. In some embodiments, one or more UV light sources can move depending on a type of the device, such as to accommodate a different device shape (e.g., a respirator versus a smartphone). One or more UV light sources may move prior to and/or during a decontamination cycle, independently or in conjunction with the cycles for individual lamps. Movement can be on a different axis (including rotating). In some embodiments, the drawer is configured to rotate the device, such as via a rotatable platform, instead of or in addition to the UV light sources moving.

According to some embodiments, the decontamination system may be configured to track the user of the device. This can be based on a scan of an employee's badge, an RFID, a barcode, and/or a Bluetooth connection to an external camera system (such as for facial recognition), a fingerprint sensor, and/or other biometric sensor. In some embodiments, the decontamination system may track the number of cycles a user has decontaminated their device. The decontamination system may be configured to log decontamination activity per user to validate that the necessary decontamination is occurring. In some embodiments, policies by shift/workday could be enforced (for example, at the beginning of a shift or after lunch, a specific cycle would be required). In some embodiments, users can be notified via an APP and/or text message that they need to decontaminate.

According to various embodiments, the decontamination system can be configured to provide information to a user, such as on a display of the decontamination system. The information can include information on the types and/or models of devices that the decontamination system is intended to decontaminate, the history of previous cleaning cycles and recommendation or requirement for the next cycle (for example, display that a device has had 10 quick sanitize cycles, and new requires or recommends the next cycle be a long sterilization cycle), the picture or info of the owner of the device being decontaminated, and/or the location of an another available decontamination system, such as when the decontamination system is not functioning or is being used.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a," "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

FIG. 1 illustrates a respirator decontaminate device 100, according to some embodiments. The device 100 can be sized to fit on a countertop and can be used by a wearer of a respirator to personally decontaminate their own device using UV radiation. For example, healthcare personnel in medical facilities, such as doctors, nurses, and aides, can personally decontaminate their own N95 respirators, post-patient contact while they wait—for example, during the time the healthcare personnel washes his or her hands.

The device 100 includes an enclosure 102 that encloses UV lamps (discussed further below) and a drawer 104 is used to load a respirator 180 into a UV irradiation chamber within the enclosure 102. The drawer 104 includes a platform 106 for placing at least one respirator 180. The drawer 104 may be mounted to the enclosure 102 via telescoping rails 108 that enable the drawer 104 to be opened and closed. A front panel 110 of the enclosure 102 includes an aperture 112 that is shaped to accommodate the platform 106 and the at least one respirator 180 positioned on the platform 106. In some embodiments, the shape of the aperture 112 may indicate the proper positioning of the respirator 180 on the platform 106. For example, the respirator may be properly positioned with its patient-facing surface 182 facing upward and the aperture 112 may match the shape of the respirator 180 when placed in its proper position on the platform 106. In some embodiments, the aperture 112 and/or drawer 104 is configured to limit the number of respirators that can be loaded into the device 100. In some embodiments, the aperture 112 and drawer 104 are configured to limit the number of respirators that can be loaded into the device 100 to just a single respirator, which can help prevent cross-contamination between respirators and can prevent a user from accidentally switching their respirator with another user's (loss of custody), which is of particular concern in medical facilities such as hospitals. In some embodiments, the drawer 104 includes a front panel 120 that is sized to cover the aperture 112 so that UV light does not escape the enclosure 102 during use.

According to some embodiments, the platform 106 may be formed as a grating that allows UV light to pass from underneath the platform to the respirator 180, as discussed further below. In some embodiments, the grating is formed of a plurality of spaced apart members 114. In some embodiments, the plurality of spaced apart members 114 are formed of a material that transmits UV light or at least a band of UV light that is selected for decontaminating the respirator. In some embodiments, the members 114 are parallel quartz rods configured to transmit UV light in the UVC band. In some embodiments, the quartz rods are mounted to mounts 118 that are, in turn, mounted to the rails 108. In some embodiments, the mounts 118 are also made of quartz or another material that transmits at least a portion of UV light.

In some embodiments, the platform 106 includes one or more respirator strap positioning members 116 that can be used to position the straps in substantially defined positions, ensuring that the straps do not fold on themselves or cover the respirator body. In some embodiments, the respirator strap positioning members 116 are four quarts posts that project from the platform 106.

The drawer 104 may include a handle or other feature that enables a user to open and close the drawer 104. In some embodiments, the drawer 104 is powered so that it can open and close under its own power. The device 100 may include a button or touchscreen for a user to provide an open/close command and the drawer 104 may open/close in response to the user's command. In some embodiments, the device 100 includes a proximity sensor that can sense a user, such as a user's hand placed near the device 100, without the user touching the device. The device may open/close in response to detecting the user without the user having to touch the device 100, which can reduce the risk of cross-contamination through touching of the device.

In some embodiments, the device 100 includes a display screen 122 for displaying information to the user. Examples of information that may be displayed include, the status of the device (e.g., that the UV lamps are warming, that the device is ready for decontamination of a respirator, that a cycle has begun, the remaining time in a cycle, that a cycle is complete, any errors, or any other suitable information). In some embodiments, the display screen 122 is a touchscreen that enables user input. In some embodiments, the device 100 includes a separate user input device, such as one or more switches, selectors, or other suitable user input device (not shown).

Figure 2:
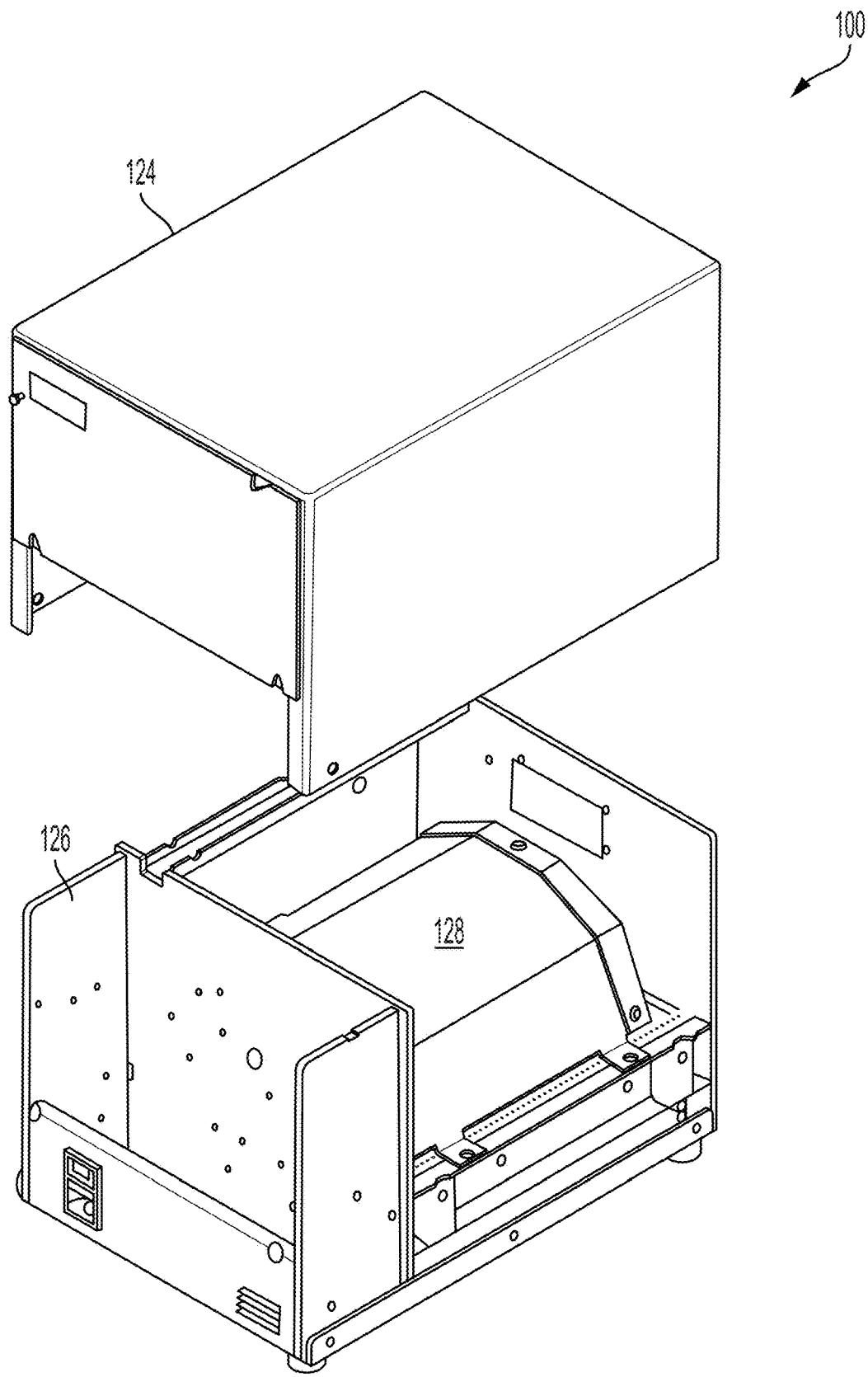
FIG. 2 illustrates is a rear view of a respirator decontaminate device with the top portion of the enclosure removed, according to various embodiments.

FIG. 2 illustrates is a rear view of the device 100 with the top portion 124 of the enclosure 102 removed, according to various embodiments. The rear portion 126 of the enclosure 102 may accommodate electrical and/or electronic components of the device 100, such as the ballast(s) for UV lamps, one or more controllers, cooling features, etc. In some embodiments, the device is actively cooled and a cooling fan, motor, or other cooling system features are located in the rear portion 126. In some embodiments, the device is passively cooled. Located centrally within the enclosure is an upper reflector 128 that defines an upper portion of the irradiation chamber where the respirator is located during the decontamination cycle. The reflector 128 can be made of various materials, including PTFE and/or highly polished aluminum.

Figure 3B:
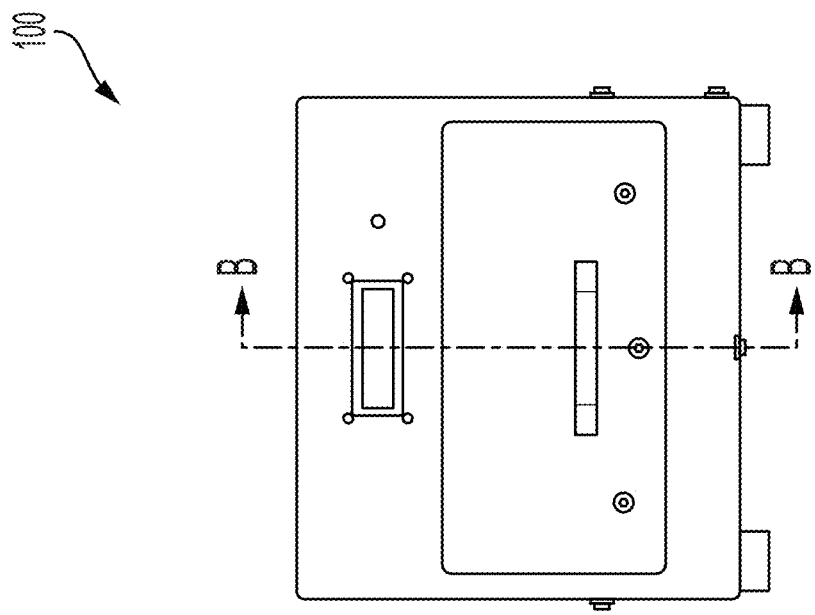
FIGS. 3A and 3B are side and front elevation views, respectively, of a respirator decontaminate device, according to various embodiments.
Figure 3A:
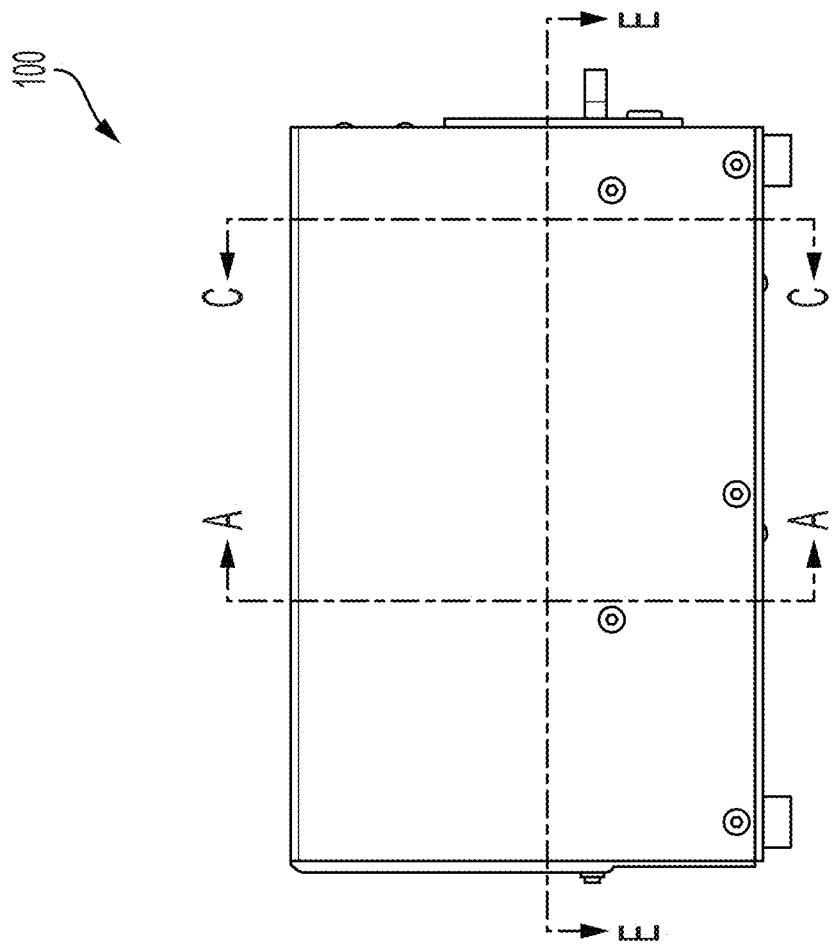

FIGS. 3A and 3B are side and front elevation views, respectively, of the device 100, illustrating the relative size of the device 100 according to various embodiments. In some embodiments, the device 100 is less than 20 inches in height and width and less than 30 inches in depth. In some embodiments, the device 100 is no more than 24 inches in depth, enabling the device 100 to fit on a standard size countertop, preferably no more than 20 inches in depth, more preferably no more than 18 inches in depth.

FIGS. 4A-4D are cross sectional views through various portions of the device of FIGS. 3A and 3B, according to various embodiments, with a respirator 180 positioned in the irradiation chamber 130. According to various embodiments, the chamber 130 may be configured to accommodate just a single respirator. This can discourage multiple respirators from being decontaminated together, which would otherwise pose risks of cross-contamination of respirators. In some embodiments, the chamber 130 is configured to accommodate more than one respirator.

A plurality of UV lamps 132 are arrayed around the irradiation chamber 130. The UV lamps 132 are illustrated in the drawings as configured as fluorescent lamps. However, the term lamp as used herein refers broadly to any artificial UV light source. Suitable UV light generating technology can include, for example, fluorescent lamps, LEDs, gas-discharge lamps, broad-spectrum light sources with filters that are separate from the lamps positioned in front of the lamps, or any suitable combination of different light sources. According to some embodiments, a lower set 132A of UV lamps are positioned in the lower portion of the irradiation chamber 130 such that they are beneath the platform 106 and an upper set 132B of UV lamps are positioned in the upper portion of the irradiation chamber 130 such that they are positioned above the platform 106. The upper reflector 128 extends around the upper set 132B of lamps in an arcuate shape to reflect light toward the outward-facing side of the respirator 180. A lower reflector 134 is positioned beneath the lower set 132A of lamps and is shaped to reflect light toward the wearer-facing side of the respirator 180.

The device 100 can include any suitable configuration of UV lamps 132. The illustrated embodiment includes four UV lamps in the upper set 132B and two UV lamps in the lower set 132A. The illustrated UV lamps each include two tubes 140 extending from a base 136. The lamps 132 are mounted in sockets 138 located toward the rear of the enclosure. The lamps 132 and upper and lower reflectors 128 and 134 may be arranged to provide UV light to all exterior surfaces of the respirator at the same time. According to some embodiments, the lamps 132 are arranged to generally uniformly irradiate the respirator. In some embodiments, the upper and lower set of lamps are the same. In other embodiments, the power of the upper set of lamps is less than the power of the lower set of lamps to account for a different in the relative number of lamps. For example, the lower set of lamps can include two 18 watt lamps and the upper set of lamps can include four 9 watt lamps, which can provide approximately a uniform irradiation of all sides of the respirator.

The UV lamps can be configured to generate a desired bandwidth of UV radiation. In some embodiments, the UV lamps generate UV light in the UVC wavelength band. In some embodiments, the UV lamps generate UVC light centered around 254 nm. In some embodiments, the lamps are doped so that UV light below 254 nm will be substantially blocked, such as to prevent the release of ozone producing 185 nm ozone producing light. The power of the lamps 132 can vary based on the number of UV lamps, the desired UV dosage, and the desired decontamination cycle time. Generally, the lower the total UV lamp power, the proportionally greater the cycle time.

According to various embodiments, the device 100 uses two 18 W UVC lamps positioned beneath the drawer and either four 18 W or four 9 W UVC lamps positioned above the drawer. Examples of suitable 18 W UVC lamps are PHILLIPS 18 W TUV PL-L 18 W/4P and OSRAM 18 W GFT18DL/2G11/SE/OF. Examples of suitable 9 W UVC lamps are PHILLIPS 9 W PL-S9W/TUV or OSRAM 9 W GCF9DS/G23/SE/OF.

According to various embodiments, the arrangement of the lamps in device, combined with the reflectors surrounding the lamps, maximizes uniformity of radiation within the irradiation chamber 130, and thus minimizes fluctuations in dose received by the various respirator surfaces. Under these conditions, it is more accurate to address the incident power density at a location on a respirator in terms of the fluence rate, rather than intensity (or irradiance), since some light can impinge on a point in the fabric of the respirator from multiple directions, including directions associated with some light backscattered from "below" (diffuse reflectance) within the respirator material. Common optical detectors respond to light intensity impinging within a solid angle of ~$\pi$ steradians (sr). So, the detector-measured values are an underestimate of the actual total exposure fluence rate, leading to a conservative estimate of the time-integrated radiant exposure, or fluence (J). The SI units for intensity and fluence rate are the same (W/m2), but fluence rate includes photons impinging from all directions over $4\pi$ steradians of solid angle, whereas intensity (irradiance) is defined as light incident from one side, over $2\pi$ (and common detectors only sense from ~$\pi$sr).

According to various embodiments, the device is configured to irradiate a respirator light at intensities at the respirator that are in the range of 5-50 mW/cm$^2$, preferably 5-40 mW/cm$^2$, more preferably 8-25 mW/cm$^2$, more preferably 10-15 mW/cm$^2$. In some embodiments, the device is configured to irradiate a respirator with 11-14 mW/cm$^2$.

Figure 4A:
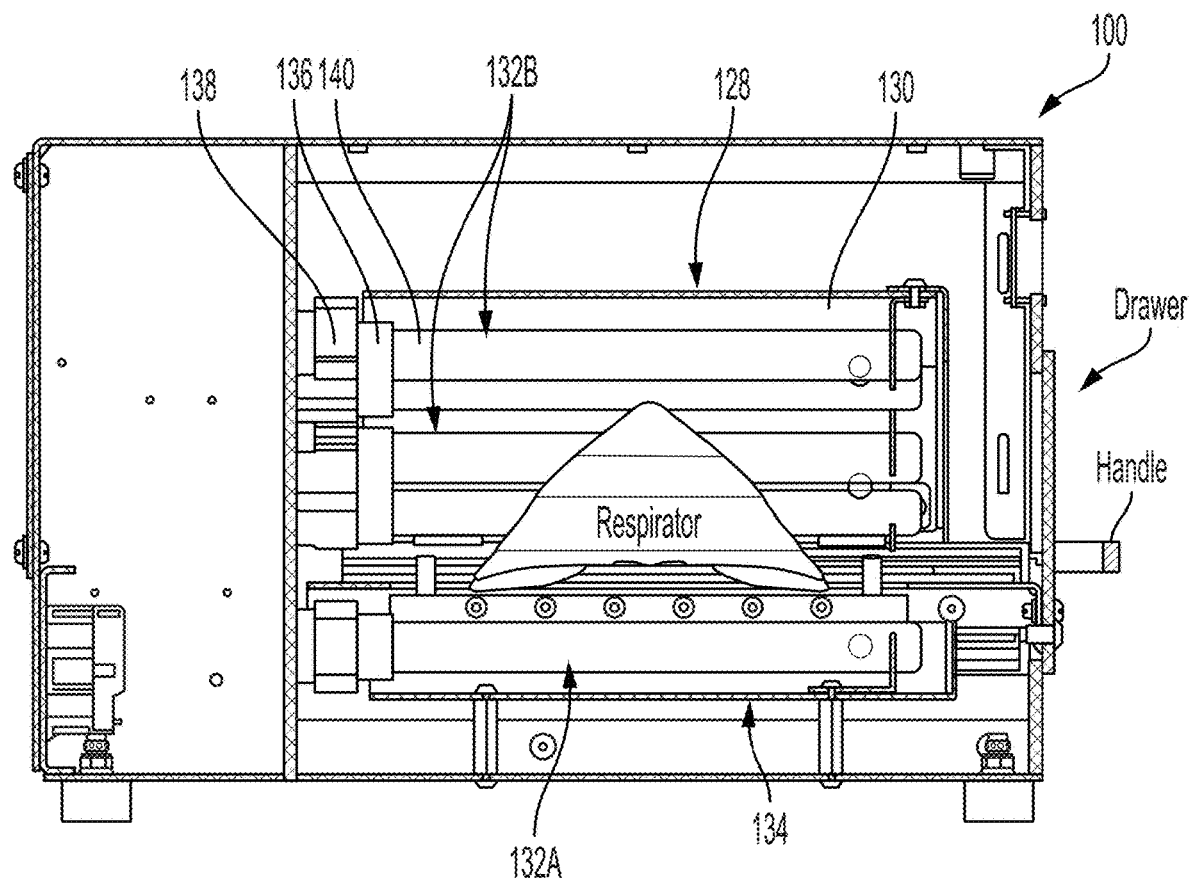
FIGS. 4A-4D are cross sectional views through various portions of a respirator decontaminate device, according to various embodiments.
Figure 4B:
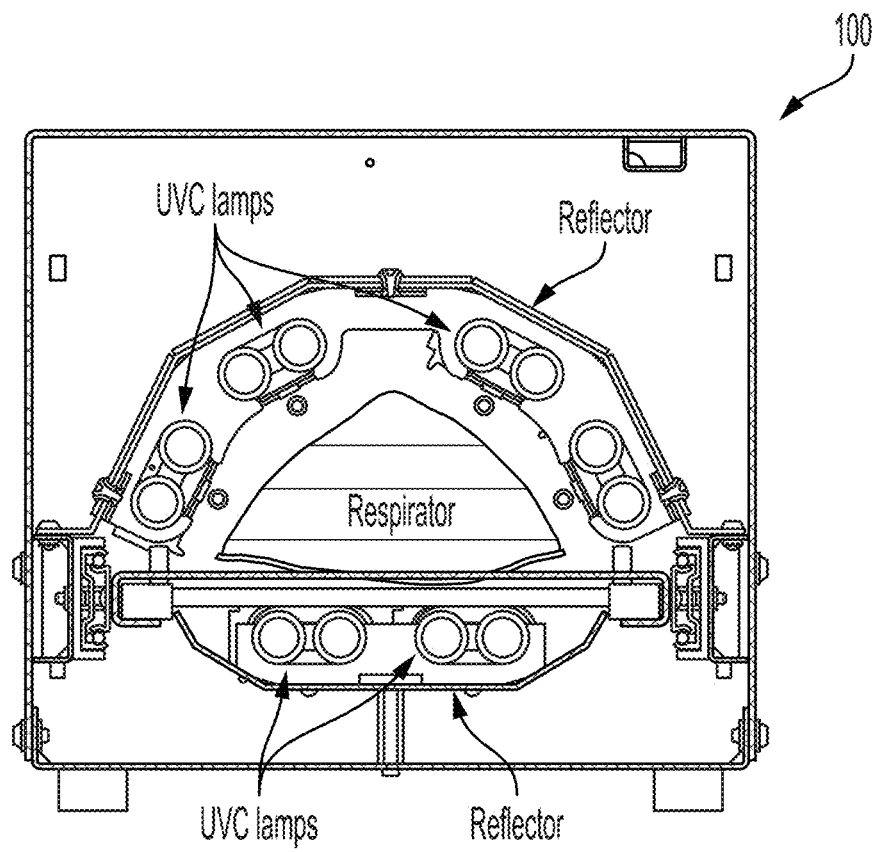
Figure 4C:
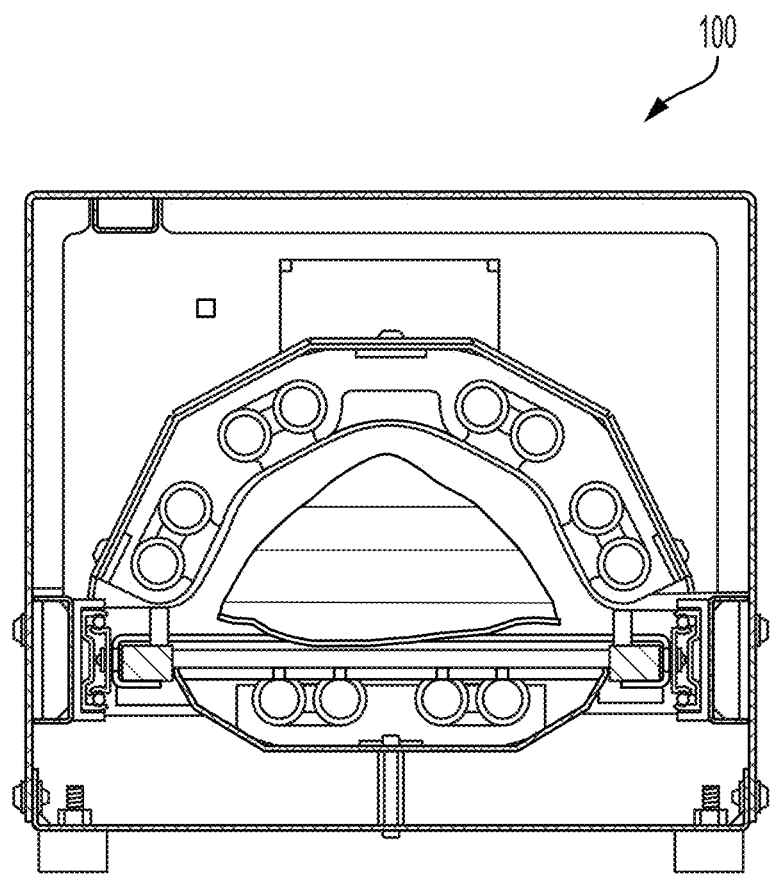
Figure 4D:
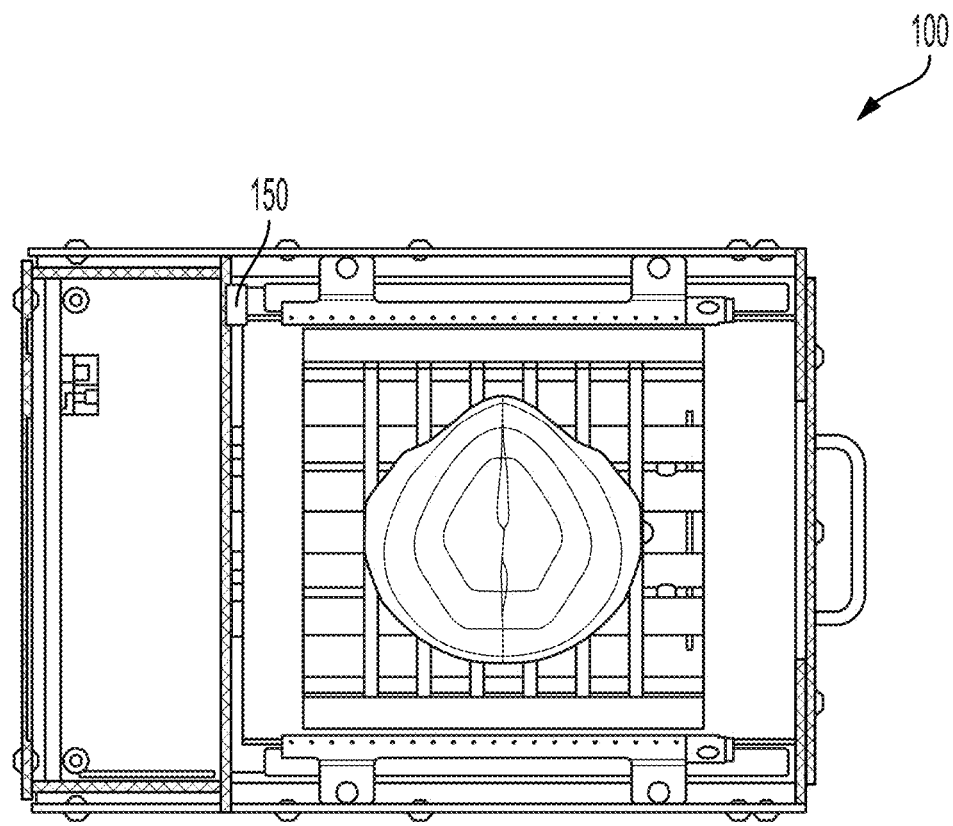

FIG. 4D illustrates a detector 150 for detecting that the drawer 104 is in a closed position. In some embodiments, the detector 150 is a magnetic switch that detects when the drawer 104 is closed and may also provide a small holding force to the drawer 104 in the closed position.

Figure 5:
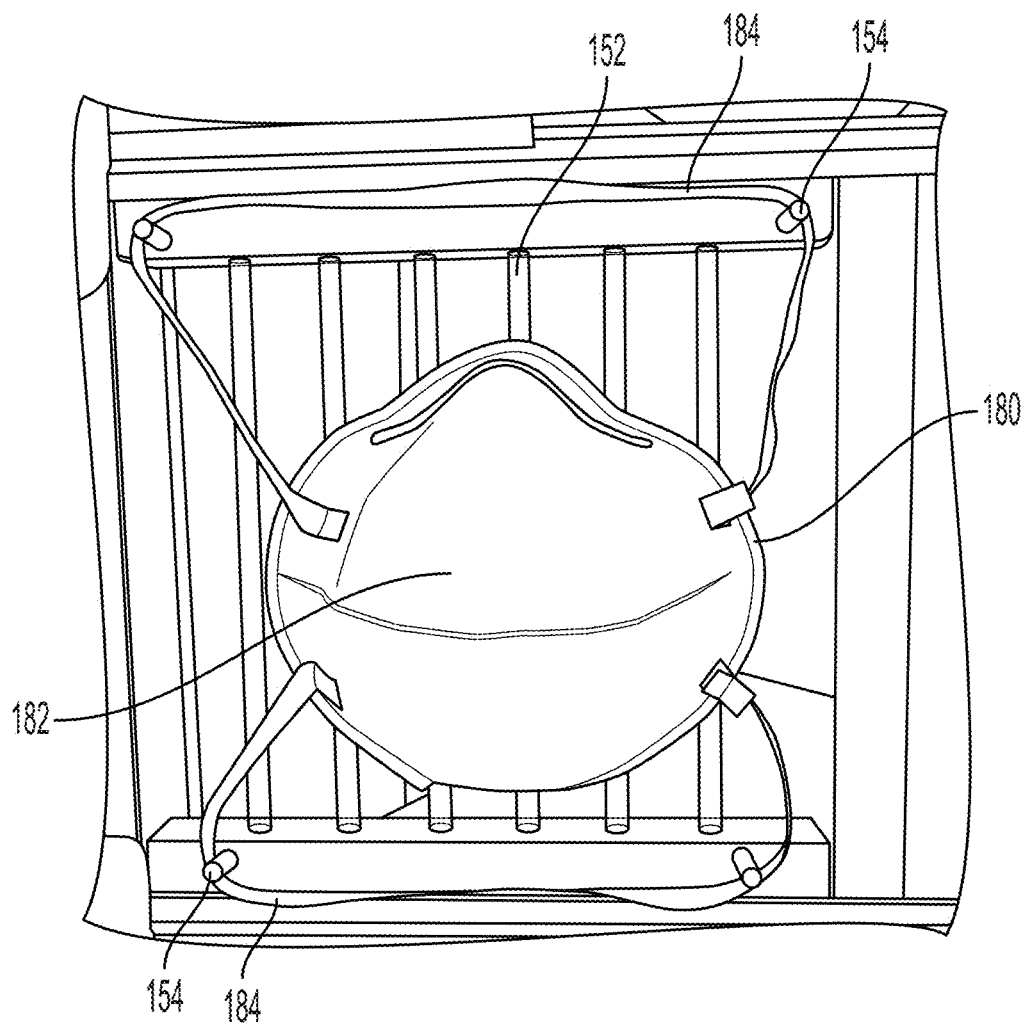
FIG. 5 illustrates the loading of a respirator on the platform of the drawer of a respirator decontaminate device, according to various embodiments.

FIG. 5 illustrates the loading of a respirator 180 on the platform 106 of the drawer 104, according to various embodiments. The respirator 180 is positioned with its wear-facing surface on quartz rods 152 of the platform 106. The straps 184 of the respirator 180 are positioned around quartz posts 154 located at the four corners of the drawer 104.

Figure 6:
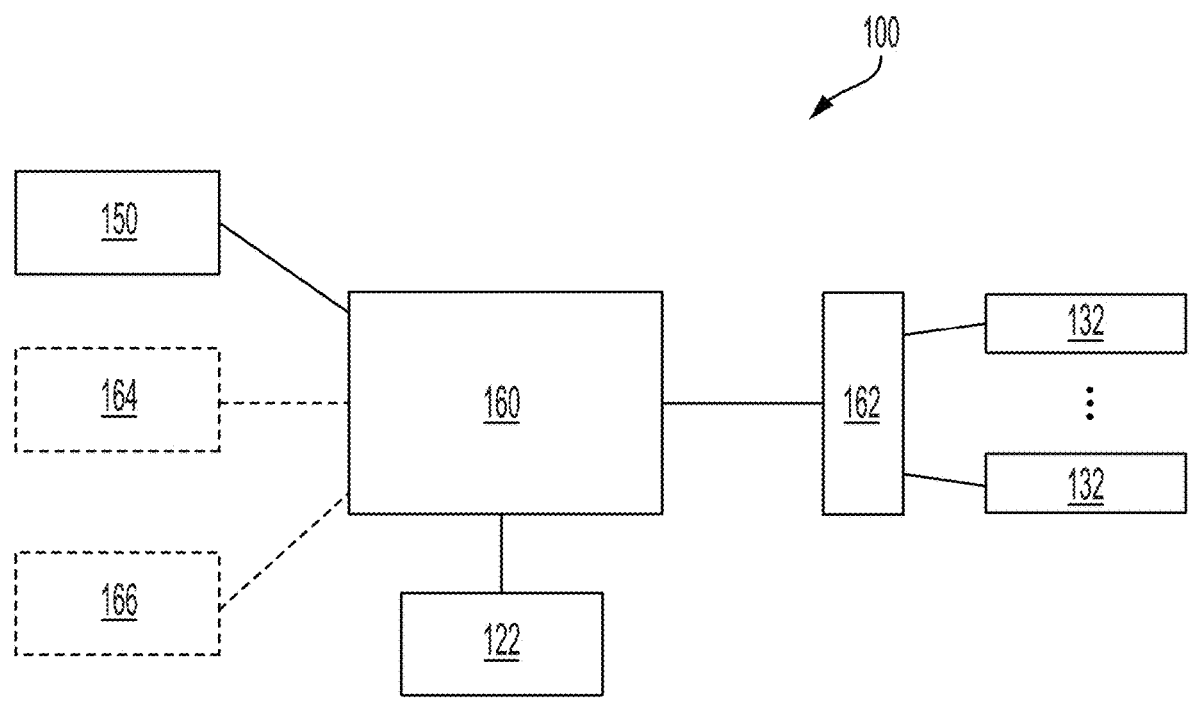
FIG. 6 is a functional block diagram of device 100, according to various embodiments.

FIG. 6 is a functional block diagram of device 100, according to various embodiments. The device 100 includes a controller 160 that activates and deactivates the UV lamps 132 vie one or more lamp drivers 162 (such as ballasts) that each drive one or more UV lamps 132. The controller includes one or more processor, memory, and one or more programs stored in the memory for execution by the one or more processors for controlling the device 100, such as according to the methods described further below.

The controller 160 is communicatively coupled to a drawer positional detector 150 that detects when the drawer is in its closed position. The controller 160 may control the activation/deactivation of the lamps 132 based on signals from the detector 150, as discussed further below. For example, the controller 160 may start or stop a decontamination cycle based on the detector 150 detecting that the drawer is in its closed position or has moved away from its closed position.

In some embodiments, the device 100 includes one or more UV sensors 164 for sensing the UV intensity in the irradiation chamber. According to various embodiments, the controller 160 may use the information from the UV sensor 164 as a diagnostic to determine whether the UV irradiation is within an acceptable level and/or may adjust a decontamination cycle time to ensure that a predefined minimum UV dosage is delivered to the respirator.

Figure 7A:
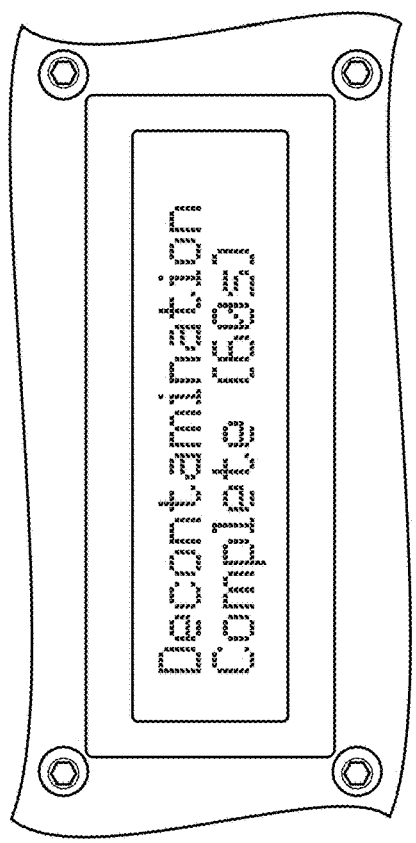
FIGS. 7A and 7B illustrate examples of information that can be displayed to the user.
Figure 7B:
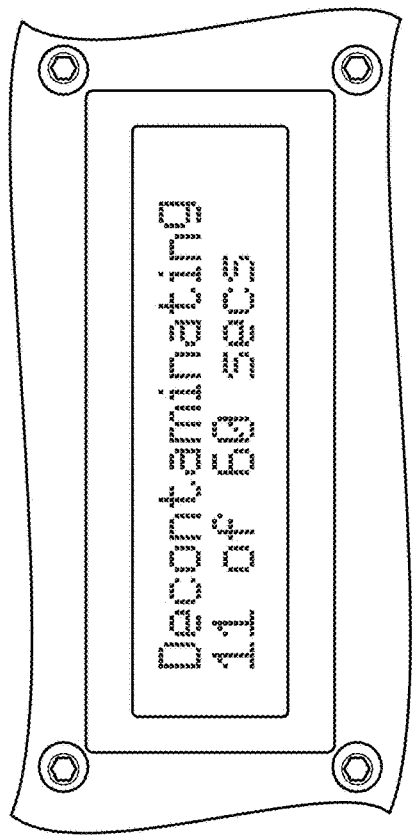

The device 100 includes a display 122 for displaying information to a user. Examples of suitable information include the readiness of the device 100, that the device is performing a decontamination cycle, the amount of time that has elapsed or is remaining in a cycle, the completion of a cycle, the cumulative usage of the lamps, and/or any other useful information. FIGS. 7A and 7B illustrate examples of information that can be displayed to the user, with the display in FIG. 7A showing that the decontamination cycle is in progress with 11 of 60 seconds having elapsed and the display of FIG. 7B showing that the 60 second decontamination cycle is complete. In some embodiments, the device 100 includes one or more user inputs 166, which can be used for various purposes, such as to initiate a decontamination cycle, to select information for viewing on the display, for altering one or more decontamination cycle parameters, such as cycle time, or for any other suitable purpose.

According to various embodiments, the controller 160 activates and deactivates the UV lamps 132 based on the input from the detector 150 and a pre-programmed decontamination cycle time. The pre-programmed cycle may automatically begin when the drawer 104 is closed. The controller 160 may automatically activate the lamps 132 and initiate a cycle timer. The controller 160 may display the amount of cycle time remaining to the user on the display 122. Once the preset cycle time has elapsed, the lamps 132 may be automatically deactivated by the controller 160 and an indication that the cycle is complete may be displayed on the display 122. In some embodiments, the drawer locks during the cycle time to prevent a person from opening the drawer while the lamps are activated. In some embodiments, the door does not lock but should it be opened at any point during a cycle, the lamps are automatically deactivated in response to the detector 150 detecting that the drawer has moved from its closed position. In some embodiments, the controller 160 tracks the total number of hours of use of the lamps and can display this information to the user via the display.

In some embodiments, the controller 160 is configured to detect a failure in a lamp and provide an indication of the failure, which can be, for example, provided on the display and/or can be provided to an external system via a network connection. In some embodiments, the controller 160 is configured to alter a cycle time based on a detected lamp failure and/or lamp degradation. For example, where the lamps are determined by the controller 160 to be delivering half their rated UV light output, the controller 160 may double the cycle time.

According to various embodiments, the device executes a decontamination cycle any time the drawer is closed (and the device is powered on). Therefore, according to various embodiments, the only user action required for using the device is closing and opening the drawer. According to various embodiments, any time the drawer is closed, the lamps will activate for only the preset cycle period, after which they will deactivate. Therefore, the lamps will not be continuously active for more than a single cycle period. In other words, the lamps will not operate continuously and will not be continuously activate for more than a single pre-programmed cycle period.

According to various embodiments, the device 100 decontaminates N95 respirators by supplying a sufficient amount of UVC germicidal irradiation. UVC (254 nm) light can deactivate viruses by cleaving RNA and/or DNA. In particular, studies have shown that 1 J/cm$^2$ of UVC light on the exterior surfaces of the respirator can provide greater than 3-log reduction in the viral load on N95 respirators. According to various embodiments, the device 100 is configured to provide a dosage of 1 J/cm$^2$ of UV light to all exterior surfaces of a single N95 respirator. In some embodiments the dosage is provided in under 10 minutes, preferably in under 5 minutes, more preferably in under 2 minutes, more preferably in a minute or less.

According to various embodiments, a method of decontaminating a respirator includes the user doffing the user's own N95 respirator and inspecting the respirator for visible signs of damage or contamination by excessive mucous, blood, or other soiling. If the respirator is visibly damaged or soiled, then the respirator should be discarded. If the respirator is not visibly damaged or soiled, the user places the respirator on the platform of the drawer of the device, such as device 100, with the outer-facing surface of the respirator facing upward. If the drawer of the device is closed, the user first opens the drawer, such as using the drawer handle. To avoid cross contamination from touching the drawer handle, the user can use a disposable tissue, wipe, or glove to grasp the handle. The user places each strap of the respirator around two respective quartz posts, which keeps the straps from folding or covering any portion of the respirator during UV irradiation. The user closes the drawer of the device, such as using a disposable tissue or with gloves. In some embodiments, the closing of the drawer is detected and the decontamination cycle is automatically initiated via activation of the UV lamps. In various embodiments, the drawer may not lock during the decontamination cycle but should the user open the drawer the UV lamps may be automatically deactivated by the controller, ensuring that the user is not exposed to UV light.

According to various embodiments, the LUV Device may be pre-programmed with the cycle time required for delivering a dosage of 1 J/cm$^2$ or less of UVC irradiation to the respirator given the UVC lamp configuration. According to various embodiments, the device tracks the amount of time remaining in the cycle and may indicate the remaining time (or elapsed time) to the user on the display screen, including when the cycle is complete. The controller may automatically deactivate the UV lamps at the end of the cycle. Upon observing that the cycle is complete, the user can open the drawer, such as by grasping the drawer handle with a disposable tissue, wipe, or glove to avoid cross contamination from the drawer handle. The user retrieves the decontaminated respirator and follows standard precautionary measures to reuse the respirator. The drawer can remain open for the next use. Should the drawer be closed, the lamps may activate for only the pre-programmed cycle period and then deactivate until the next use.

In some embodiments, the device includes a powered drawer that opens and closes without user force. The user may press a button or otherwise provide a user command that causes the drawer to close and/or open. In some embodiments, upon the completion of a decontamination cycle, the drawer may automatically open for the user to retrieve the respirator.

According to various embodiments, the decontamination device can be configured to provide a UVC dosage to all portions of the exterior surfaces of a respirator of at least 0.1 J/cm$^2$, preferably at least 0.3 J/cm$^2$, more preferably at least 0.5 J/cm$^2$, more preferably at least 0.9 J/cm$^2$. In some embodiments, the decontamination device can be configured to provide a UVC dosage to all portions of the exterior surfaces of a respirator of less than 10 J/cm$^2$, preferably less than 3 J/cm$^2$, more preferably less than 1.5 J/cm$^2$, more preferably less no more than 1 J/cm². In some embodiments, the device is configured to provide a dosage of UVC effective to decontaminate a respirator of one or more target pathogens in less than 10 minutes, preferably less than 5 minutes, more preferably less than 2 minutes, and more preferably no more than 1 minute. In some embodiments, the device is configured to decontaminate a respirator of one or more target pathogens by delivering a dosage of UVC light to all surfaces of the respirator that is effective to provide at least a 3-log reduction of at least one enveloped virus, such as SARS-CoV-2, more preferably, at least one non-enveloped virus. In some embodiments, the device is capable of providing a dosage of UVC light of 1 J/cm² in 1 minute or less.

According to various embodiments, the device 100 may include network communication technology, which can include wired and/or wireless network communication capability, and can be connected to a network, such as a hospital internal network, a cloud network, or any other suitable network. According to various embodiments, the device 100 can receive software updates via the network connection, can receive user commands via the network (such as through an APP on a user's smartphone), can upload usage statistics, operational status, errors codes, or other information to a server system, and/or communicate any other suitable information.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A filtering facepiece respirator decontamination device comprising:
   an enclosure defining an ultraviolet (UV) irradiation chamber;
   UV lamps positioned in the irradiation chamber;
   a moveable drawer comprising a platform for positioning a respirator, wherein the moveable drawer can move to a closed position in which the respirator positioned on the platform is located in the irradiation chamber;
   a front opening through which the respirator passes when the respirator is positioned on the platform and the drawer closes, wherein the front opening is shaped to indicate the proper positioning of the respirator on the platform, wherein the proper positioning comprises an outer-facing surface of the respirator facing an upward direction and an inner-facing surface of the respirator facing a downward direction, and wherein the front opening matches a shape of the respirator;
   a switch for detecting that the drawer is in the closed position; and
   a controller for activating the plurality of UV lamps based on the switch detecting that the drawer is in the closed position,
   wherein at least a portion of the UV lamps are arrayed above the moveable drawer in an arcuate shape that corresponds to the shape of the respirator.

2. The device of claim 1, wherein a second set of the UV lamps is positioned beneath the drawer.

3. The device of claim 1, wherein the device includes at least one reflector surrounding the at least a portion of the UV lamps for reflecting UV light toward the respirator.

4. The device of claim 1 wherein the platform comprises a plurality of quartz rods.

5. The device of claim 4, wherein the drawer comprises a plurality of quartz posts that project from the platform for locating straps of the respirator.

6. The device of claim 1, wherein the device is configured to accommodate only a single respirator at a time.

7. The device of claim 1, wherein the device is configured to deliver a UV dosage to the respirator of 1 J/cm² in one minute or less.

8. The device of claim 1, wherein the controller is configured to activate the UV lamps automatically in response to receiving a signal from the switch indicating that the drawer is in the closed position.

9. The device of claim 8, wherein the controller is configured to deactivate the UV lamps automatically in response to receiving a signal from the switch indicating that the drawer has moved away from the closed position.

10. The device of claim 1, wherein the UV lamps are configured for generating UVC light.

11. A method of decontaminating a filtering facepiece respirator comprising:
    positioning the respirator on a platform of a drawer of a filtering facepiece respirator decontamination device that comprises an enclosure defining a UV irradiation chamber and a front opening shaped to indicate an outer-facing surface of the respirator faces an upward direction and an inner-facing surface of the respirator faces a downward direction, and wherein the front opening matches a shape of the respirator;
    closing the drawer such that the respirator is located in the irradiation chamber;
    activating, by a controller of the device, UV lamps of the device based on a switch of the device detecting that the drawer has been closed, wherein at least a portion of the UV lamps are arrayed above the moveable drawer in an arcuate shape that corresponds to the shape of the respirator; and
    deactivating, by the controller the device, the UV lamps after a pre-programmed decontamination period has elapsed.

12. The method of claim 11, comprising delivering a dosage of UV light of 1 J/cm² to the respirator.

13. The method of claim 11, wherein the pre-programmed decontamination period is a minute or less.

14. The method of claim 11, further comprising, in response to detecting that the drawer has been opened while the UV lamps are activated, automatically deactivating the UV lamps.

15. The method of claim 11, wherein the UV lamps generate UVC light.

* * * * *